United States Patent
Kitajima

[11] Patent Number: 5,132,837
[45] Date of Patent: Jul. 21, 1992

[54] OPERATION MICROSCOPE
[75] Inventor: Nobuaki Kitajima, Tokyo, Japan
[73] Assignee: Kabushiki Kaisha Topcon, Tokyo, Japan
[21] Appl. No.: 492,150
[22] Filed: Mar. 13, 1990
[30] Foreign Application Priority Data
  Mar. 17, 1989 [JP] Japan .................. 1-31054[U]
[51] Int. Cl.$^5$ .................. G02B 21/22; G02B 27/22
[52] U.S. Cl. .................. 359/374; 359/368; 359/473
[58] Field of Search .................. 33/261, 276–277; 351/205; 350/507–528, 537–544, 574, 130–143; 359/368–390, 462–477

[56] References Cited

U.S. PATENT DOCUMENTS

| 1,864,895 | 6/1932 | Egy | 350/512 |
| 1,985,073 | 12/1934 | Bauersfeld | 350/511 |
| 3,734,593 | 5/1973 | Mori | 350/515 |
| 4,290,666 | 9/1981 | Rüdel | 350/522 |
| 4,440,475 | 4/1984 | Colliaux | 350/511 |
| 4,527,869 | 7/1985 | Nihoshi | 350/511 |
| 4,619,503 | 10/1986 | Reinheimer et al. | 350/511 |
| 4,714,327 | 12/1987 | Marshall | 350/511 |
| 4,872,052 | 10/1989 | Liudzius et al. | 350/515 |

FOREIGN PATENT DOCUMENTS

| 394514 | 11/1908 | France | 350/557 |
| 57-102607 | 6/1982 | Japan . | |

Primary Examiner—Bruce Y. Arnold
Assistant Examiner—Thong Nguyen
Attorney, Agent, or Firm—Armstrong & Kubovcik

[57] ABSTRACT

An operation microscope including a plurality of objective lenses arranged at different angles with respect to an object to be viewed and a selecting optical system having a function of selecting one of light beams from the objective lenses and enabling the object to be observed at the different angles. Accordingly, a visual field for observation of an object to be operated may be expanded.

2 Claims, 2 Drawing Sheets

OPERATION MICROSCOPE

BACKGROUND OF THE INVENTION

The present invention relates to an operation microscope for use in operation of ophthalmology, orthopedics, etc., and more particularly to an operation microscope which can change an observation angle with respect to an affected part as an object to be operated.

A conventional operation microscope for use in ophthalmologic operation, for example, is normally provided with a microscope body including a main lens-barrel for a person in charge of operation and an auxiliary lens-barrel for another person assisting the person in charge. The auxiliary lens-barrel is mounted integrally with the main lens-barrel, or it is detachably mounted to the main lens-barrel. Each of the main lens-barrel and the auxiliary lens-barrel contains an objective optical system, a variable power optical system and an image forming optical system.

Such an operation microscope is effective in the ophthalmologic operation since both the person in charge and the assistant person can observe the same affected part at the same time.

However, in the case of the above-mentioned operation microscope, an optical axis of the main lens-barrel and an optical axis of the auxiliary lens-barrel are fixed though there are some different types such that an angle of the former with respect to the affected part is the same as or different (0-30 degrees) from an angle of the latter.

Therefore, there is a problem that a visual field to the object to be operated is fixed in a range as defined by the optical axis of the main lens-barrel and the auxiliary lens-barrel which are preliminarily set.

The present invention has been achieved as taking the above circumstances into consideration, and it is an object of the present invention to provide an operation microscope which may expand a visual field for observation of an object to be operated.

It is another object of the present invention to provide an operation microscope which may enable a person to observe the light beams advancing from different directions at different positions.

It is a further object of the present invention to provide an operation microscope which may enable a person to observe the light beams advancing from different directions at a fixed position.

SUMMARY OF THE INVENTION

According to the present invention, there is provided an operation microscope comprising a plurality of objective lenses arranged at different angles with respect to an object to be operated and a selecting optical system having a function of selecting one of light beams from said objective lenses and enabling said object to be observed at said different angles.

The selecting optical system is located behind the objective lenses and between the objective lenses and an image formation point.

A light beam from at least one of the objective lenses and a light beam from the other objective lenses have image formation points at different positions.

With this construction of the present invention, as the plural objective lenses are arranged at different angles with respect to the object to be operated, and one of the light beams from the objective lenses is selected by the selecting optical system to be observed, a visual field for observation of the object to be operated can be expanded by the suitable select operation of the selecting optical system.

DESCRIPTION OF THE PREFERRED EMBODIMENTS

Figure 1:
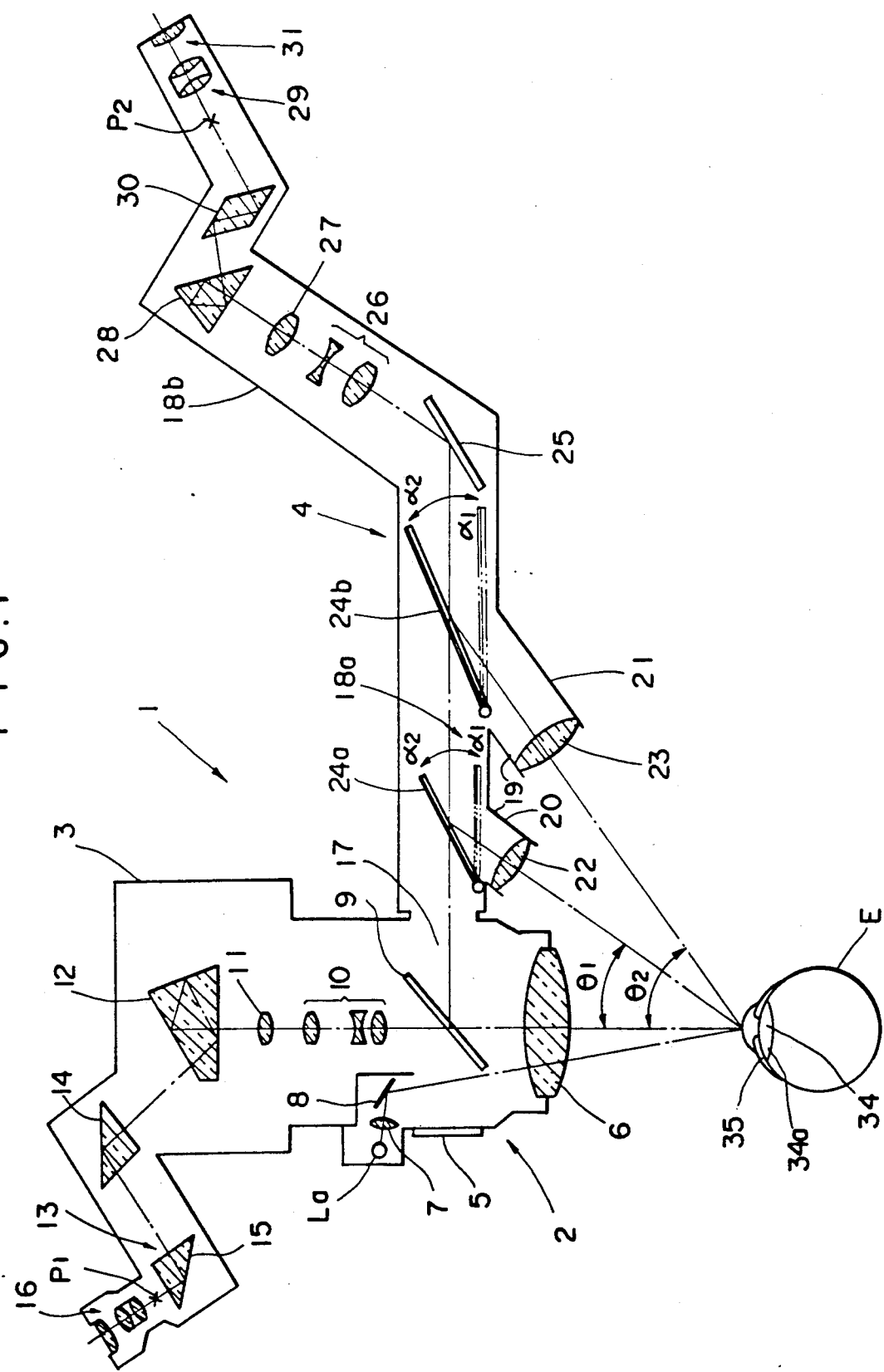
FIG. 1 is a schematic illustration of a preferred embodiment of the operation microscope of the present invention.

An operation microscope 1 as shown in FIG. 1 includes a microscope body 2 constructed of a main lens-barrel 3 for a person in charge of operation (which will be hereinafter referred to as "operator"), an auxiliary lens-barrel 4 for a person assisting the operator (which will be hereinafter referred to as "assistant"), and a mounting member 5 for rotatably mounting the auxiliary lens-barrel 4 to the main lens-barrel 3.

The microscope body 2 is connected to a hanging arm of a microscope stand not shown, and it is vertically movable over an eye E as an object to be operated.

The main lens-barrel 3 is formed in a substantially cylindrical shape, and is provided at its lower end portion with an objective lens 6 as an objective optical system. The objective lens 6 can be replaced by another one having a focal length according to a depth of an affected part to be operated.

The main lens-barrel 3 is further provided with an illumination light source La, a lens 7 and a reflecting mirror 8. Light emitted from the illumination light source La is collected by the lens 7, and is then reflected by the reflecting mirror 8. The reflected light is introduced to the objective lens 6, and is then irradiated onto the eye E as the object to be operated.

The main lens-barrel 3 is further provided with a semitransparent mirror 9 over the objective lens 6, a variable power optical system 10 for providing an afocal variable power for an image to be observed. Further, an ocular optical system 13 is mounted over the main lens-barrel 3.

The ocular optical system 13 includes an image forming lens 11, an erect prism 12, a reflecting mirror 14 for reflecting a light beam from the erect prism 12, a prism 15 for total-reflecting a light beam from the reflecting mirror 14, and an ocular system 16, whereby an erect image of the eye E can be formed at an image formation point $P_1$ for observation.

A side wall portion of the main lens-barrel 3 where the semi-transparent mirror 9 is located is cut away along the circumference of the main lens-barrel 3, so as to form an opening 17 for mounting the auxiliary lens-barrel 4.

The auxiliary lens-barrel 4 includes a horizontal cylindrical portion 18a retained under a horizontal condition by the mounting member 5 to the main lens-barrel 3 and rotatably mounted thereto, and an inclined cylindrical portion 18b projecting inclinedly upwardly from an outer end of the horizontal cylindrical portion 18a.

The horizontal cylindrical portion 18a of the auxiliary lens-barrel 4 is opened at its inner end (an end on the side of the main lens-barrel 3) so as to be communicated with the opening 17.

There is installed in the horizontal cylindrical portion 18a a selecting optical system 19 for selecting one of light beams entering at different angles from the eye E and introducing the selected light beam to an observing position.

The selecting optical system 19 includes first and second cylindrical portions 20 and 21 projecting from a lower side of the horizontal cylindrical portion 18a toward the eye E, first and second objective lenses 22 and 23 mounted in the first and second cylindrical portions 20 and 21 in such a manner as to have respective optical axis inclined at respective angles $\theta_1$ and $\theta_2$ with respect to an optical axis of the objective lens 6, a first reflecting member 24a located in the horizontal cylindrical portion 18a in the vicinity of the first objective lens 22 in such a manner as to be rotatable in opposite directions as depicted by arrows $\alpha_1$ and $\alpha_2$, for selecting either of the light beam from the semi-transparent mirror 9 or the light beam from the first objective lens 22 and introducing the selected light beam to the inclined cylindrical portion 18b, a second reflecting member 24b located in the horizontal cylindrical portion 18a in the vicinity of the second objective lens 23 in such a manner as to be rotatable in opposite directions as depicted by arrows $\alpha_1$ and $\alpha_2$, for selecting one of the light beams from the semi-transparent mirror 9, the first reflecting member 24a and the second objective lens 23 and introducing the selected light beam to the inclined cylindrical portion 18b, and a boundary reflecting member 25 located in a boundary region between the horizontal cylindrical portion 18a and the inclined cylindrical portion 18b for reflecting the light beam advancing in the horizontal cylindrical portion 18a to the inclined cylindrical portion 18b.

The first and second objective lenses 22 and 23 have respective focal lengths as focusing at the position of the eye E.

There are installed in the inclined cylindrical portion 18b a variable power optical system 26 for providing an afocal variable power over the boundary reflecting member 25.

The inclined cylindrical portion 18b is further provided at its upper end portion with an ocular optical system 29 for the assistant. The ocular optical system 29 includes an image forming lens 27, an erect prism 28, a prism 30 for changing an optical path and an ocular portion 31, whereby an image of the eye E can be formed at an image formation point $P_2$ for observation.

The operation of the operation microscope 1 mentioned above will now be described in the case of conducting the operation on the eye E.

The light from the illumination light source La is irradiated through the lens 7, the reflecting mirror 8 and the objective lens 6 to the eye E.

A reflected light beam from the eye E is collimated by the objective lens 6 in the main lens-barrel 3, and is divided by the semi-transparent mirror 9 into a light beam advancing in the main lens-barrel 3 and a light beam advancing into the auxiliary lens-barrel 4.

The light beam advancing in the main lens-barrel 3 is varied in power by the variable power optical system 10, and is then focused by the image forming lens 11. Thereafter, the image is converted into an erect image by the erect prism 12, and the light beam advances via the reflecting mirror 14 and the prism 15 to form an image at the image formation point $P_1$.

The operator can observe the image at the image formation point $P_1$, that is, the image of the eye E through the ocular system 16; however, he cannot see from this image an end region 34a of a crystal lens 34 to be shut off by an iris 35 of the eye E.

On the other hand, when both the first and second reflecting members 24a and 24b are disposed at the positions shown by alternate long and two short dashes lines in FIG. 1, the light beam advancing from the semi-transparent mirror 9 into the horizontal cylindrical portion 18a is introduced to the boundary reflecting member 25, and is reflected by the boundary reflecting member 25, then being introduced to the variable power optical system 26. After being varied in power by the variable power optical system 26, the light beam is focused by the image forming lens 27, and the image is converted into an erect image by the erect prism 28. Then, the optical path of the light beam is changed by the prism 30 to form an image at the image formation point $P_2$.

The assistant can observe the image at the image formation point $P_2$, that is, the image of the eye E through the ocular portion 31 at an angle substantially the same as the angle of observation by the operator.

In the case that the first reflecting member 24a is rotated in the direction of the arrow $\alpha_2$, and the second reflecting member 24b is maintained at the position shown by the alternate long and two short dashes line in FIG. 1, the operator can observe the image as similar to the case mentioned above, while the assistant can observe the image of the eye E at an angle different by $\theta_1$ from the angle of observation by the operator.

In this case, the light beam from the eye E is collimated by the first objective lens 22, and is then reflected by the first reflecting member 24a to be introduced to the boundary reflecting member 25. Thereafter, the light beam advances along a path as similar to the case mentioned above, and the image is formed at the image formation point $P_2$ for observation by the assistant.

Accordingly, the assistant can observe the end region 34a of the crystal lens 34 which can not be observed by the operator.

In the case that the second reflecting member 24b is rotated in the direction of the arrow $\alpha_2$ from the above position so as to shut off the light beam from the first reflecting member 24a, the assistant can observe the image of the eye E at an angle different by $\theta_2$ from the angle of observation by the operator. In this case, as the angle $\theta_2$ is greater than the angle $\theta_1$, the assistant can observe the end region 34a of the crystal lens 34 more deeply than the above case where the angle of observation is $\theta_1$.

By the operation of the auxiliary lens-barrel 4 as mentioned above, the skilled assistant may give the operator a suitable advice or the like during the operation on the eye E.

Further, as the auxiliary lens-barrel 4 can be rotated around the main lens-barrel 3 through the mounting member 5, a visual field to the eye E can be more expanded by rotating the auxiliary lens-barrel 4 as required.

Figure 2:
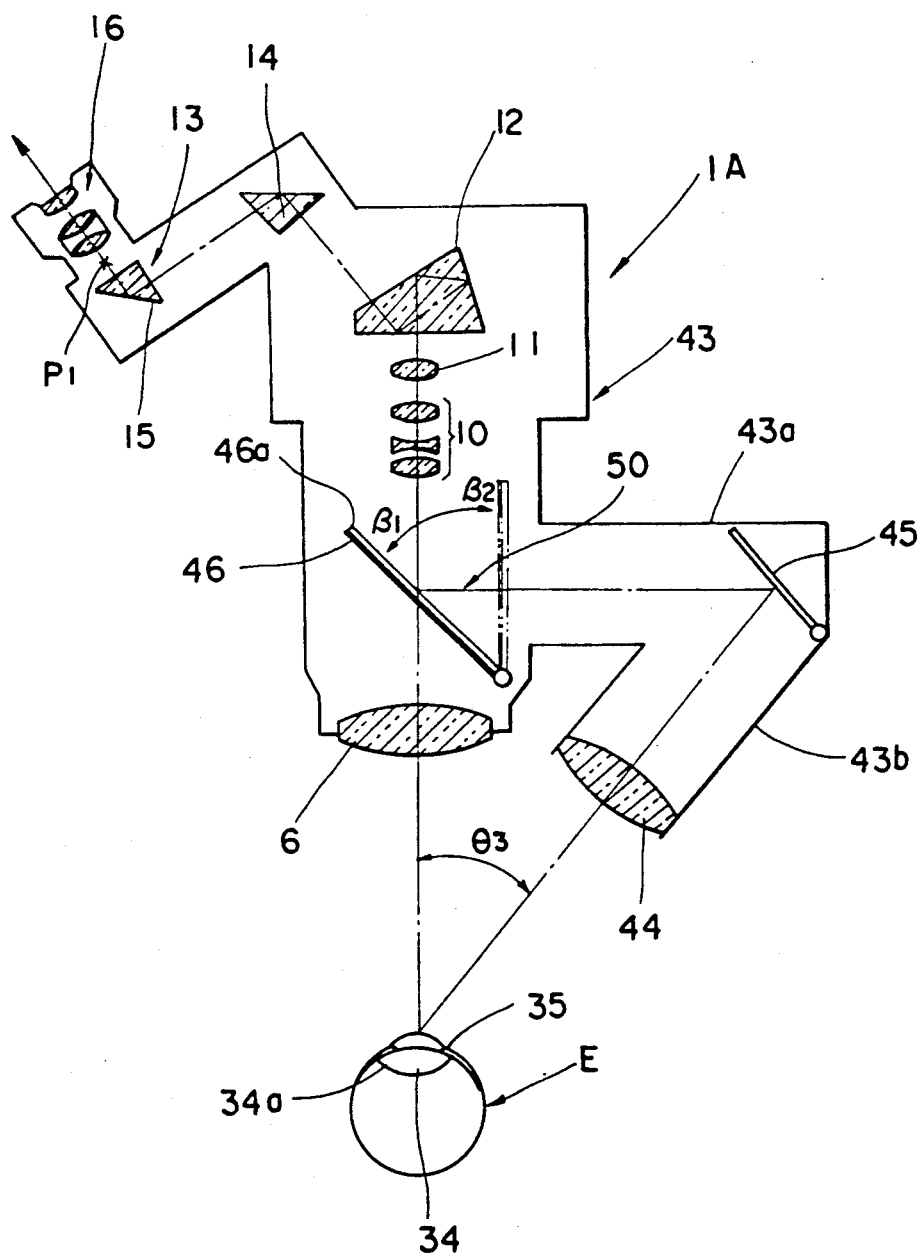
FIG. 2 is a schematic illustration of another preferred embodiment of the operation microscope of the present invention.

There will now be described a second preferred embodiment of the present invention with reference to FIG. 2. In an operation microscope 1A as shown in FIG. 2, elements having the same functions as those of the operation microscope 1 shown in FIG. 1 are designated by the same reference numerals, and the explanation thereof will be omitted hereinafter.

The operation microscope 1A is characterized in that a main lens-barrel 43 only is provided, and that a first objective lens 6 and a second objective lens 44 are installed in the main lens-barrel 43 at different angles with respect to the eye E, and that a selecting optical system 50 is installed between the objective lens 6 and the variable power optical system 10.

The main lens-barrel 43 includes a horizontal projecting cylindrical portion 43a projecting from a side wall of the main lens-barrel 43 and an inclined projecting cylindrical portion 43b projecting from the horizontal projecting cylindrical portion 43a toward an optical axis of the main lens-barrel 43 and arranged in such a manner that an optical axis of the inclined projecting cylindrical portion 43b is inclined at an angle $\theta_3$ from the optical axis of the objective lens 6. The second objective lens 44 is mounted at a projecting end of the inclined projecting cylindrical portion 43b.

The selecting optical system 50 includes a reflecting mirror (first reflecting member) 45 located at a boundary between the horizontal projecting cylindrical portion 43a and the inclined projecting cylindrical portion 43b and a second reflecting member 46 located between the objective lens 6 and the variable power optical system 10 in such a manner as to be rotatable in opposite directions as depicted by arrows $\beta_1$ and $\beta_2$.

A reflecting surface 46a of the second reflecting member 46 is opposed to the reflecting mirror 45.

The objective lens 6 and the second objective lens 44 have the same focal length such that the focus of both lenses lie at the same position.

Although not shown, the operation microscope 1A shown in FIG. 2 also includes an illuminating system constructed of an illumination light source, a lens and a reflecting mirror.

The operation of the operation microscope 1A as mentioned above will now be described.

When the second reflecting member 46 is set in a position as shown by an alternate long and two short dashes line in FIG. 2, a reflected light beam from the eye E is collimated by the objective lens 6, and is allowed to enter the variable power optical system 10 without being shut off by the second reflecting member 46. Thereafter, the light beam advances along a path as similar to the case mentioned previously, and an image of the eye E is formed at the image formation point $P_1$.

Accordingly, the operator can observe the image of the eye E as seen in elevation.

In the case that the operator rotates the second reflecting member 46 to a position shown by a solid line in FIG. 2 according to the situation of the operation, the reflected light beam from the objective lens 6 is shut off by the second reflecting member 46. However, at this time, the reflected light beam from the eye E is collimated by the second objective lens 44 having the optical axis inclined at the angle $\theta_3$ from the optical axis of the objective lens 6. Then, the light beam is reflected by the reflecting mirror 45 to enter the second reflecting member 46.

Then, the light beam reflected by the second reflecting member 46 enters the variable power optical system. Thereafter, the light beam advances along the same path as the case mentioned previously with reference to FIG. 1, and the image is formed at the image formation point $P_1$.

Accordingly, the operator can observe the image of the eye E at an angle different from that before rotating the second reflecting member 46. That is, he can observe the end region 34a of the crystal lens 34 under the iris 35. The operation of the operation microscope 1A is effective especially in case of a low contrast of the eye E.

Any modifications other than the above-mentioned preferred embodiments can be made according to the present invention.

For example, the rotating operation of the first and second reflecting members 24a and 24b and the second reflecting member 46 can be effected by manual operation with a knob or automatic operation with an electromagnetic solenoid.

Although the above-mentioned preferred embodiments employ the objective lenses of two systems or three systems, the present invention may be embodied by providing the objective lenses of more systems, e.g., four or more systems.

While the invention has been particularly shown and described in reference to preferred embodiments thereof, it will be understood by those skilled in the art that changes in form and details may be made therein without departing from the spirit and scope of the invention.

I claim:

1. An operation microscope for use in operating on an object comprising:

a light source means for irradiating light into said object;

a plurality of objective lens means arranged at different angles with respect to said object for receiving light beams reflected from said object, and for irradiating at least one of said light beams into at least one eye of an operator;

a plurality of ocular optical systems; and a selecting optical means for selecting at least one light beam reflected from said object and by moving between a position for shutting the reflected light beam and another position for guiding the reflected light beam to a corresponding one of said plurality of ocular optical systems, wherein, when said at least one reflected light beam is shut off by said selecting optical means, images at the same angles are focused on a plurality of ocular optical systems, and wherein, when said reflected light beam selected by said selecting optical means is guided to a selected ocular optical system, each of said ocular optical systems focuses an image at a different angle.

2. The microscope as defined in claim 1, wherein said selecting optical means is located behind said objective lens means, and between said objective lens means and an image formation point.

* * * * *